US008382847B2

(12) United States Patent
Wyss et al.

(10) Patent No.: US 8,382,847 B2
(45) Date of Patent: Feb. 26, 2013

(54) POSTERIOR STABILIZED KNEE WITH VARUS-VALGUS CONSTRAINT

(75) Inventors: Joe Wyss, Fort Wayne, IN (US); Terry Dietz, Columbia City, IN (US); Marc C. Vosler, Columbia City, IN (US); Don Running, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 2352 days.

(21) Appl. No.: 11/121,408

(22) Filed: May 4, 2005

(65) Prior Publication Data

US 2005/0192672 A1 Sep. 1, 2005

Related U.S. Application Data

(63) Continuation of application No. 10/242,122, filed on Sep. 12, 2002, now abandoned.

(51) Int. Cl.
*A61F 2/38* (2006.01)
(52) U.S. Cl. .................................... 623/20.27
(58) Field of Classification Search ............... 623/20.27, 623/20.24, 20.26, 20.33
See application file for complete search history.

(56) References Cited

U.S. PATENT DOCUMENTS

| 4,298,992 | A | 11/1981 | Burstein et al. |
|---|---|---|---|
| 4,634,444 | A | 1/1987 | Noiles |
| 5,007,932 | A | 4/1991 | Bekki et al. |
| 5,011,496 | A | 4/1991 | Forte et al. |
| 5,116,375 | A | 5/1992 | Hofmann |
| 5,147,405 | A | 9/1992 | Van Zile et al. |
| 5,330,532 | A | 7/1994 | Ranawat |
| 5,370,699 | A | 12/1994 | Hood et al. |
| 5,549,686 | A | 8/1996 | Johnson et al. |
| 5,658,342 | A | 8/1997 | Draganich et al. |
| 6,039,764 | A | 3/2000 | Pottenger et al. |
| 6,123,729 | A | 9/2000 | Insall et al. |
| 6,203,576 | B1 | 3/2001 | Afriat et al. |
| 6,206,926 | B1 | 3/2001 | Pappas |
| 6,325,828 | B1 | 12/2001 | Dennis et al. |
| 6,406,497 | B2 | 6/2002 | Takei |
| 6,443,991 | B1 | 9/2002 | Running |
| 6,475,241 | B2 | 11/2002 | Pappas |
| 6,558,426 | B1 | 5/2003 | Masini |

(Continued)

FOREIGN PATENT DOCUMENTS

FR 2 805 456 8/2001

OTHER PUBLICATIONS

Shuichi Matsuda, MD et al., "Knee Kinematics of Posterior Cruciate Ligament Sacrificed Total Knee Arthroplasty," *Clinical Orthopaedics & Related Research*, Aug. 1997, pp. 257-266.

(Continued)

*Primary Examiner* — Thomas J Sweet
*Assistant Examiner* — Cheryl Miller
(74) *Attorney, Agent, or Firm* — Maginot, Moore & Beck, LLP

(57) ABSTRACT

A femoral component of a knee prosthesis has spaced condyle surfaces defining a notch therebetween. The notch defines an elongated cam housing having an anterior cam and a posterior cam at opposite ends of the housing. The tibial component of the knee prosthesis includes a platform and a bearing supported on the platform, the bearing defining bearing surfaces configured to articulate with the condyle surfaces. The tibial component includes a spine projecting superiorly from the bearing that defines an anterior face and a posterior face. The posterior face and the posterior cam define complementary curved surfaces configured for cooperative engagement when the femoral component and the tibial component are at a predetermined flexion angle. The cam housing is configured to form a gap between the posterior cam and the spine when the knee is normally extended. In another feature, the spine includes a stiffening pin extending therethrough.

18 Claims, 2 Drawing Sheets

U.S. PATENT DOCUMENTS

| | | |
|---|---|---|
| 6,620,198 B2 | 9/2003 | Burstein et al. |
| 6,699,291 B1 | 3/2004 | Augoyard et al. |
| 2003/0009232 A1 | 1/2003 | Metzger et al. |

OTHER PUBLICATIONS

James B. Stiehl, M.D. et al., "In Vivo Determination of Condylar Lift-off and Screw-Home in a Mobile-Bearing Total Knee Arthroplasty," *Journal of Arthroplasty*, vol. 14, No. 3, 1999, pp. 293-299.

John C. Gardiner, PhD, et al., "Strain in the Human Medial Collateral Ligament During Valgus Loading of the Knee," *Clinical Orthopaedics and Related Research*, No. 391, 2001, pp. 266-274.

Jose Romero, MD, et al., "Varus and Valgus Flexion Laxity of Total Knee Alignment Methods in Loaded Cadaveric Knees," *Clinical Orthopaedics and Related Research*, No. 394, 2002, pp. 243-253.

John N. Insall, M.D., et al., "Correlation Between Condylar Lift-Off and Femoral Component Alignment," *Clinical Orthopaedics and Related Research*, No. 403, 2002, pp. 143-152.

Hiroshi Johima, MD, et al., "Effect of Tibial Slope or Posterior Cruciate Ligament Release on Knee Kinematics," *Clinical Orthopaedics and Related Research.*, No. 426, 2004, pp. 194-198.

Sang Yang Lee, MD, et al., "A Posterior-Stabilized Total Knee Arthroplasty Shows Condylar Lift-off during Deep Knee Bends," *Clinical Orthopaedics and Related Research*. No. 435, 2005, pp. 181-184.

P.F.C. Sigma RP Knee System, DePuy Orthopaedics, Inc.

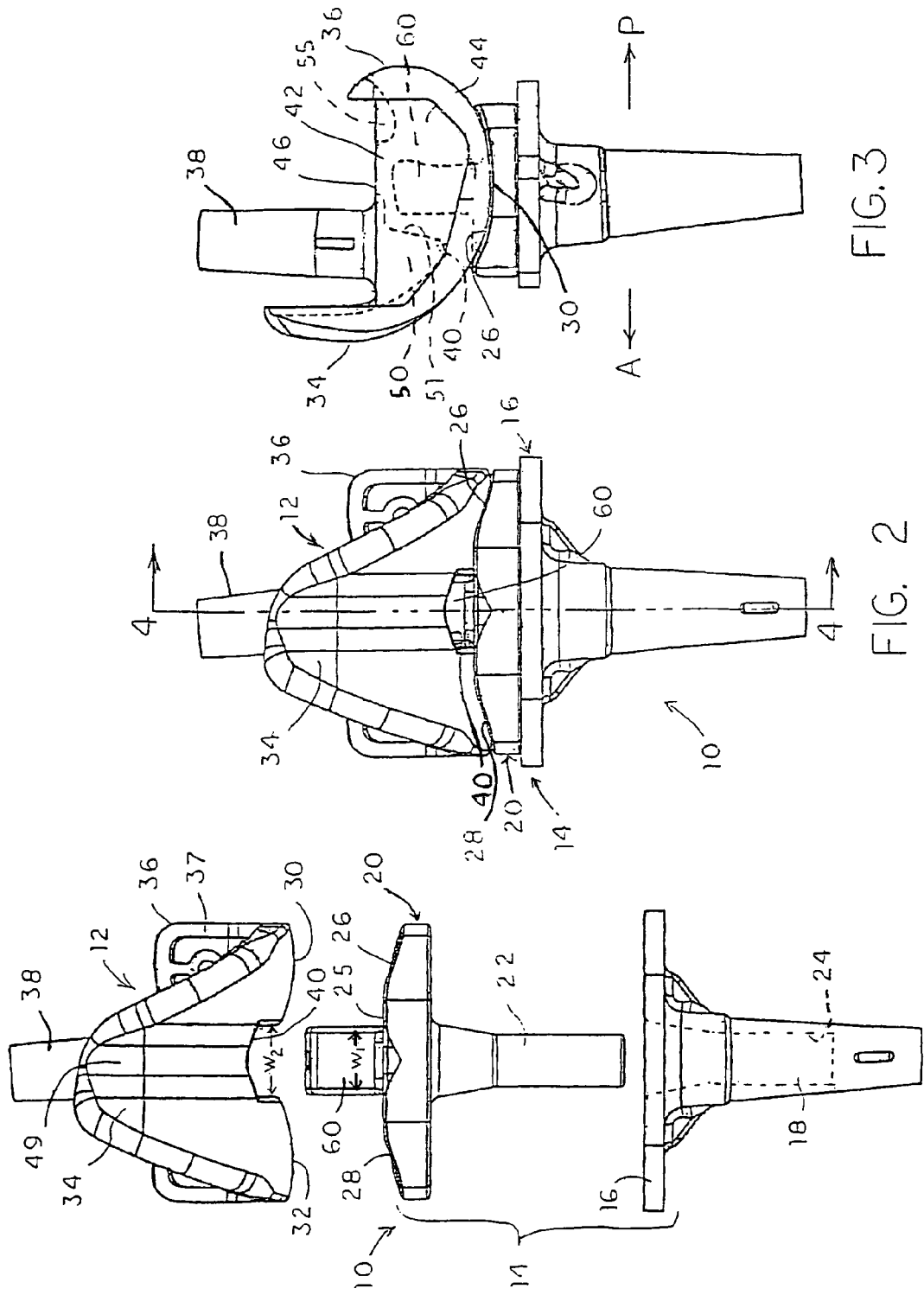

POSTERIOR STABILIZED KNEE WITH VARUS-VALGUS CONSTRAINT

This application is a continuation of application Ser. No. 10/242,122, filed on Sep. 12, 2002 now abandoned, the disclosure of which is hereby totally incorporated by reference in its entirety.

BACKGROUND OF THE INVENTION

The present invention relates to a knee prosthesis and more particularly to a mobile bearing knee providing posterior stabilization of the anterior-posterior translation of the femoral component relative to the tibial component.

Flexion and extension of the normal human knee involves complex movements of the femur, the tibia and the patella. During flexion (i.e., when the knee is bent), the distal end of the femur and the proximal end of the tibia roll and glide relative to each other, with the center of rotation of the joint moving posteriorly over the condyles of the femur. This complex movement is typically referred to as rollback. During extension (i.e., when the leg is straightened), the tibia and femur follow a reverse path. Simultaneous with the movements of the tibia and femur, the patella moves over the surface of the femoral condyles, while remaining a constant distance from the tubercle of the tibia.

Damage or disease can deteriorate the bones, articular cartilage and ligaments of the knee, which can ultimately affect the ability of the natural knee to function properly. To address these conditions, prosthetic knees have been developed that are mounted to prepared ends of the femur and tibia. Among the many knee prostheses, a mobile bearing knee simulates the condylar and bearing surfaces of the knee to emulate the natural movement of the knee during flexion and extension. The tibial component is configured to permit rotation about the axis of the tibia to accurately replicate the effects of differential rollback in the transverse plane.

In one type of mobile bearing knee, the tibial component includes an upward projecting spine that translates within an intercondylar notch formed in the femoral component, The spine can contact cam surfaces at the anterior and posterior ends of the notch to limit the relative anterior-posterior movement between the two bones. The spine also operates to provide varus-valgus stability of the joint and to resist dislocation or subluxation at high angles of flexion. An exemplary mobile bearing knee is disclosed in U.S. Pat. No. 6,443,991, the disclosure of which is incorporated herein by reference. Other exemplary mobile bearing knees are embodied in the LCS™ System and the PFC Sigma RP™ knee system marketed by Depuy Orthopaedics, Inc., of Warsaw, Ind.

While mobile bearing knees are thought to most accurately mimic the natural movement of the intact knee, the design of knee systems requires the introduction of features to maintain the stability of the artificial joint. Thus, modern knee systems provide additional stability to posterior stabilized devices to prevent hyperextension. The articulating and rotating components of the knee system must do so smoothly and accurately. At the same time, the natural knee permits a certain amount of movement and pivoting in the transverse and coronal planes that should be approximated in the prosthetic knee system. The development of knee systems has attempted to harmonize the need for preserving a full range of motion with the need for maintaining the strength of the joint.

SUMMARY OF THE INVENTION

The present invention contemplates an improved knee prosthesis comprising a femoral component configured to be attached to the distal end of a femur and having a medial and a lateral condyle surface spaced apart to define a notch therebetween. The notch defines an elongated cam housing having an anterior cam and a posterior cam at opposite ends of the cam housing.

The prosthesis further includes a tibial component including a platform configured for attachment to the proximal end of a tibia and a bearing supported on the platform. The bearing defines medial and lateral bearing surfaces configured to articulate with the medial and lateral condyle surfaces, and a spine projecting superiorly from the bearing within the cam housing when the condyle surfaces are in articulating contact with the bearing surfaces.

The spine defines an anterior face facing the anterior cam and a posterior face facing the posterior cam. In one feature of the invention, the posterior face and the posterior cam defining complementary curved surfaces configured for cooperative engagement when the femoral component and the tibial component are rotated relative to each other to at least a predetermined flexion angle. In certain embodiments, that predetermined angle corresponds to about 50° of flexion of the knee joint.

The complementary curved surfaces of the posterior cam and posterior face of the spine are preferably curved at a common radius, while the anterior cam and the anterior face of the spine are substantially flat.

In one aspect of the knee prosthesis the cam housing defines a width sufficient to provide a predetermined clearance on either side of the spine, when the spine projects into the cam housing, to limit varus-valgus movement or pivoting of the joint. In a preferred embodiment, the widths of the spine and cam housing are sized to limit varus-valgus pivoting to 0.5°-1.5°.

In addition, the cam housing can be configured so that a gap exists between the posterior cam and the spine when the knee is in its normally extended position. The spine does not contact the posterior cam until the knee is flexed to the predetermined angle. In another aspect, the complementary surfaces of the spine and posterior cam do not nest or coincide until the knee is flexed further to another predetermined angle. The posterior cam can include a blunt or rounded anterior end that contacts the spine first when the knee is flexed. The spine and posterior cam produce roll-back for the knee prosthesis.

In yet another aspect of the invention, the spine has a greater height than prior spine designs. The spine height is calibrated to prevent subluxation of the joint at high flexion angles. In a preferred embodiment, the spine height is about 24.6 mm. The cam housing includes a roof that is sized relative to the condyle surfaces so that the spine cannot contact the roof when the condyle surfaces are supported on the bearing surfaces.

The invention also contemplates a knee prosthesis comprising a femoral component configured to be attached to the distal end of a femur and having a medial and a lateral condyle surface spaced apart to define a notch therebetween, the notch defining an elongated cam housing having an anterior cam and a posterior cam at opposite ends of the cam housing. The prosthesis also comprises a tibial component including a platform configured for attachment to the proximal end of a tibia and a bearing supported on the platform, the bearing defining medial and lateral bearing surfaces configured to articulate with the medial and lateral condyle surfaces, and a spine projecting superiorly within the cam housing when the condyle surfaces are in articulating contact with the bearing surfaces, wherein the spine defines an anterior face facing the anterior cam and a posterior face facing the posterior cam and configured for cooperative engagement when the posterior cam.

In this embodiment, the spine further defines a bore therethrough that receives a pin configured to be disposed within the bore. The pin is formed of a material different from the material of the spine to add stiffness or bending strength to the spine. The pin can be configured to be press-fit into the bore. In certain embodiments, the spine is formed of a plastic and the pin is formed of a metal.

In still another aspect of the invention, a knee prosthesis comprises a femoral component configured to be attached to the distal end of a femur and having a medial and a lateral condyle surface spaced apart to define a notch therebetween, the notch defining an elongated cam housing having an anterior cam and a posterior cam at opposite ends of the cam housing. A tibial component includes a platform configured for attachment to the proximal end of a tibia and a bearing supported on the platform, the bearing defining medial and lateral bearing surfaces configured for rotating contact with the medial and lateral condyle surfaces. A spine projects superiorly from the bearing within the cam housing when the condyle surfaces are in articulating contact with the bearing surfaces, the spine defining an anterior face facing the anterior cam and a posterior face adapted for articulating contact with the posterior cam.

With this embodiment, the cam housing is configured to define an anterior-posterior distance between the anterior cam and the posterior face of the spine when the femoral component and the tibial component are in a normally extended position relative to each other. With this configuration, the posterior face of the spine is in articulating contact with the posterior cam only at a first predetermined flexion rotation angle between the femoral component and the tibial component. In a specific embodiment, the first predetermined flexion angle is about 50°.

This embodiment further contemplates that the posterior cam and the posterior face define complementary curved surfaces, whereby the complementary surfaces articulate relative to each other at flexion angles between the femoral component and the tibial component greater than the first predetermined flexion angle. The posterior cam can include a rounded anterior end that is arranged to contact the posterior face first at the first predetermined flexion angle. The complementary curved surface of the posterior cam can further be arranged on the posterior cam so that complementary curved surface of the posterior cam is substantially nested within the complementary curved surface of the posterior face of the spine only after the femoral component and the tibial component rotate relative to each other to a second predetermined flexion angle greater than the first predetermined flexion angle.

It is one object of the present invention to provide a prosthetic knee that accurately and efficiently emulates the kinematics and function of a normal, health knee. A more specific object is to accomplish these functions with a posterior stabilized knee that can create proper joint roll-back.

Another object is accomplished by features of the invention that restrict varus-valgus movement or pivoting, as well as provide resistance to subluxation. Other objects and certain benefits of the invention can be appreciated from the following written description together with the accompanying figures.

DESCRIPTION OF THE FIGURES

FIG. 1 is an exploded side view of a mobile bearing knee system according to one embodiment of the present invention.

FIG. 2 is an anterior view of the knee system shown in FIG. 1.

FIG. 3 is a lateral view of the knee system shown in FIGS. 1 and 2.

FIG. 4c includes a partial cut-away of the spine on the bearing.

DESCRIPTION OF THE PREFERRED EMBODIMENT

Figure 5:
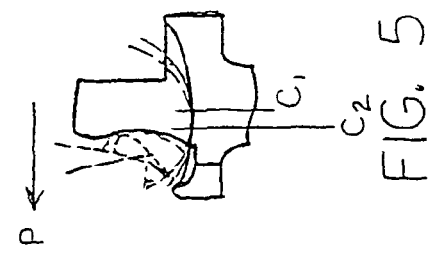
FIG. 5 is an enlarged diagram illustrating roll-back of the contact point between the femoral and tibial components of the mobile bearing knee system shown in FIG. 4c.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Referring to FIG. 1, a knee system 10 is depicted that includes a femoral component 12 and a tibial component 14. The tibial component includes a tibial platform 16 from which extends a tibial stem 18 that is configured for engagement within the prepared end of the tibia. A bearing 20 is rotatably mounted on the platform 16 by way of a bearing stem 22 that fits within a complementary socket 24 within the platform.

The bearing 20 defines an upper bearing surface that supports the femoral component. More specifically, the bearing 20 includes a lateral bearing surface 26 and a medial bearing surface 28. These bearing surfaces 26, 28 are configured for articulating support of corresponding condyle bearings 30, 32 of the femoral component 12. This articulating or sliding support is best seen in FIGS. 2 and 3.

The femoral component 12 is configured to emulate the configuration of the femoral condyles. Thus, the component 12 includes an anterior portion 34 and a posterior portion 36 that are curved in the manner of the natural condyles. The anterior portion 34 defines a patellar groove 49 that is configured to orient a patellar implant (not shown) in a manner known in the art.

The femoral component 12 utilizes a number of surfaces to fix the component to the prepared end of the femur. The inner surface 37 of the anterior and posterior portions 34, 36, are configured to directly interface over the prepared end of the femur. In addition, a stem 38 can be provided that is fixed within the femur. In addition, the femoral component 12 can include an intercondylar notch 40 formed by a pair of opposite side walls 44 and a roof 46.

As thus far described, the prosthetic knee 10 can assume a variety of known configurations. For instance, the femoral component 12 and tibial component 14 as described above can have the configuration of like components of the mobile bearing knee described in U.S. Pat. No. 6,443,991, the description of which is incorporated by reference.

As with the prior mobile bearing knee of the '991 patent, the knee 10 of the present invention includes a spine 60 that projects from the upper surface 25 of the bearing 20. The spine 60 resides within a cam housing 42 (FIG. 3) that is essentially formed by the walls of the intercondylar notch 40. In one aspect of the present invention, the spine 60 is sized relative to the cam housing 42 to provide a measured degree of varus-valgus constraint. The spine 60 has a width $W_1$ that is slightly less than the width $W_2$ of the cam housing 42 at the intercondylar notch 40 (FIG. 1). These two widths are sized relative to each other to limit varus-valgus movement or pivoting to a range of about 0.5°-2.5°. In a specific preferred embodiment of the invention, the width $W_1$ is sized relative to the width $W_2$ to provide 0.13 mm clearance on each side of the spine. Preferably, this clearance should be limited to from about 0.12 mm to about 0.50 mm per side to avoid excessive varus-valgus movement of the knee components 12, 14 relative to each other. In the specific embodiment, this clearance permits about 1.25° of varus-valgus pivoting.

As with other known prosthetic knees, each of the components must be sized to the skeletal dimensions of the patient. Thus, it is contemplated that the femoral component 12 and tibial component 14 can be provided in several sizes, and preferably in six sizes ranging from small to extra-large. For a medium sized knee, the tibial spine 60 can have a width $W_1$ of about 17.5 mm. In accordance with the specific embodiment discussed above (i.e., with a 0.13 mm clearance on each side), the cam housing 42 would have a width $W_2$ of 17.76 mm to provide the proper side-to-side clearance for the spine 60. The dimensions of the spine and the cam housing can be appropriately proportioned for other sizes of knee components.

Figure 4C:
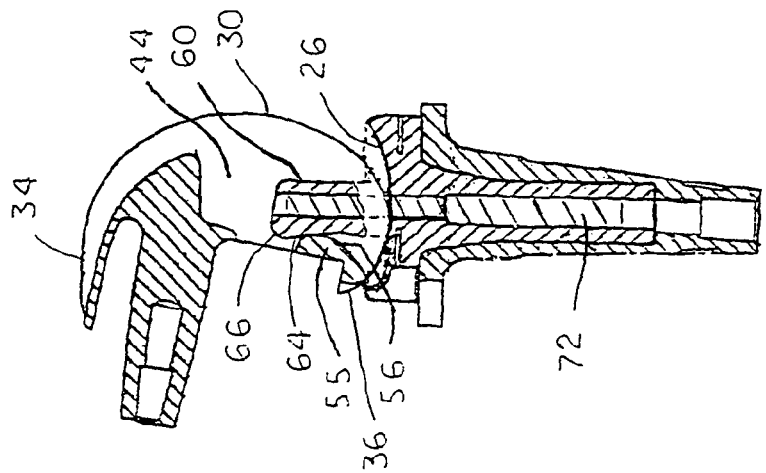
FIGS. 4a-4c are cross-sectional view of the knee system shown in FIG. 2, taken along line 4-4, with the knee system shown in its hyper-extended, normally extended, and flexed configurations.
Figure 4B:
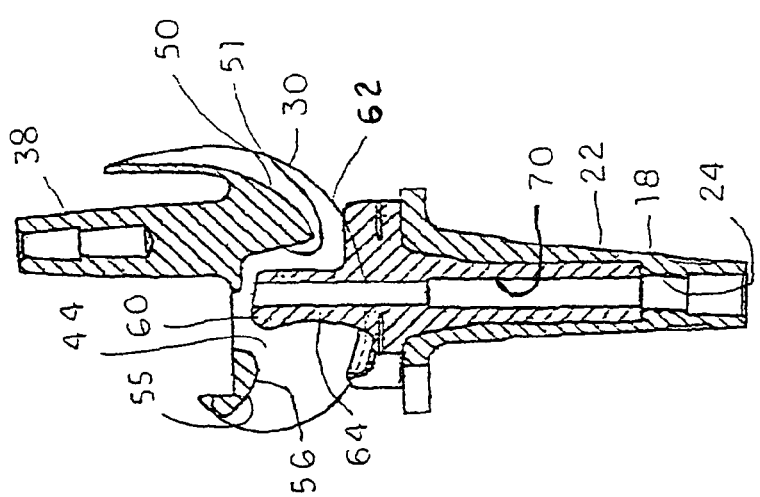

In addition to providing a measured degree of varus-valgus constraint, the spine 60 interacts with the cam housing 42 to prevent subluxation of the knee 10. In particular, the spine 60 defines a subluxation height from the bearing surface 25 that corresponds to the distance that the femoral component must be raised relative to the tibial component until the femoral component is clear of the top of the spine. Subluxation is generally not a problem when the knee is straightened (as shown in FIGS. 3 and 4b), but can be problematic when the knee is flexed (as shown in FIG. 4c). Thus, the subluxation height is measured at a certain degree of flexion, most typically at 120° of flexion. (For comparison, the knee in FIG. 4c is shown at approximately 80° of flexion).

In accordance with the preferred embodiment of the present invention, the spine has an effective height of between 16-24 mm, and most preferably 19.3 mm, when the prosthesis is at 90° flexion. Thus, the femoral component must rise off the tibial bearing 20 by at least 19.3 mm to cause a dislocation of the knee. The natural ligaments and surrounding soft tissues of the knee provide sufficient resistance to femoral lift-off greater than this subluxation height, especially at high flexion angles.

Figure 4A:
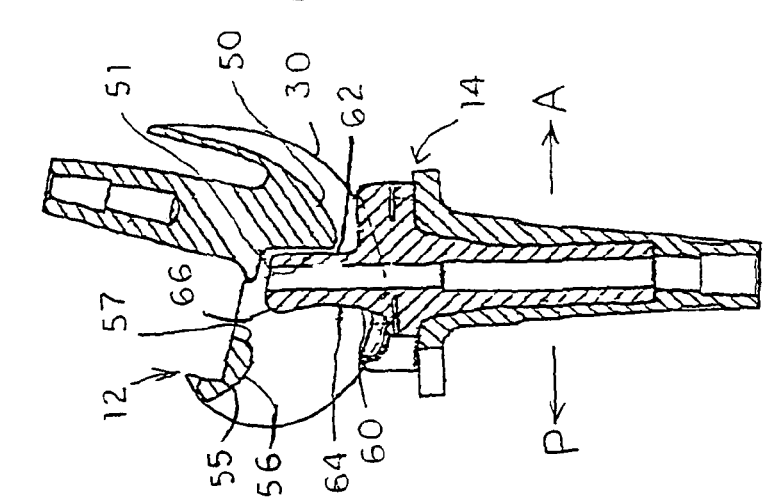

Referring now to FIGS. 3 and 4a-c, a further feature of the present invention is depicted. In particular, the cam housing 42 defines an anterior cam 50 having a cam face 51. This anterior cam 50 is adjacent the anterior portion 34 of the tibial component 12. As seen in FIGS. 3 and 4a, the cam face 51 is substantially flat. Similarly, the spine 60 has an anterior face 62 that is also substantially flat. The cam face 51 and anterior face 62 are arranged to restrict extension of the knee in the anterior direction (as designated by the arrow A in FIG. 4a). Thus, as the tibia, and hence the tibial component 14, moves anteriorly relative to the femur and femoral component 12, the spine 60 can contact the anterior cam 50 to prevent further movement in the anterior direction. In the illustrated embodiment, this contact can occur at about 5° hyperextension. However, tension in the ligaments supporting and surrounding the knee will prevent hyper-extension of the knee, and ideally will prevent contact between the spine and the anterior cam 50.

The cam housing further defines a posterior cam 55 at the opposite end of the intercondylar notch 40 from the anterior cam 50, as shown in FIG. 3. The posterior cam 55 defines a curved surface 56 that cooperates with a curved posterior face 64 of the spine, as best shown in FIG. 4c. These cooperating surfaces are configured for optimum roll-back characteristics of the prosthetic knee 10. As the knee is flexed from the neutral position depicted in FIG. 4b to the position shown in FIG. 4c, it is desirable for the contact point between the tibial and femoral components, as well as the axis of rotation of the tibia relative to the femur, to shift posteriorly (as designated by the direction arrow P in FIG. 4a). This posterior shift optimizes the moment arm and reduces the strain on the quadricep muscle responsible for flexing the knee.

As shown in FIG. 4b, the cam housing 42 is elongated between the anterior and posterior cams so that the bearing 20, and particularly the spine 60, can articulate as the knee is initially flexed and the condyle bearings 30, 32 rotate on the bearing surfaces 26, 28. As the knee continues to rotate to about 50° of flexion, the posterior face 64 of the spine 60 contacts the posterior cam 55. This contact between spine and cam provides posterior stability to the knee 10 as the knee continues to flex. In order to accommodate continued femoral roll-back, the mating surfaces are complementary curved, as best illustrated in FIGS. 4a-4b. Specifically, the posterior face 64 of the spine 60 is concave from the bearing surface 25 of the bearing 20 to the posterior peak 66 at the top of the spine. The posteriorly directed peak 66 provides additional posterior stability and resistance to subluxation at high flexion angles of 120° and beyond.

The curvature or concavity of the posterior face 64 is selected to permit a predetermined amount of roll-back, while maintaining the posterior stability afforded by the spine-to-cam contact. This roll-back is depicted in FIG. 5. The contact point designated $C_1$ corresponds to the initial contact between the spine and the posterior cam. When the knee is flexed further, the contact point shifts posteriorly to the contact point $C_2$. In a preferred embodiment, the posterior face 64 is configured to permit roll-back of between 0.0 mm up to about 5.0 mm. Most preferably this roll-back is about 4.2 mm. Thus, as the knee continues to flex from the 50° point of contact between spine and posterior cam, the curved surface 56 of the cam nestles into the curved posterior face 64. At the same time, the contact point between the femoral component 12 and the tibial component 14 shifts posteriorly. Continued flexing causes the curved cam surface 56 to articulate within the concave posterior face 64 of the spine, which further shifts the contact point in the posterior direction.

In a preferred embodiment, the curved posterior face 64 of the spine 60 is concave at a radius of between 28-32 mm. Most preferably, the radius of the posterior face is about 30 mm. The curved posterior face 64 transitions into the posterior peak 66, which is preferably rounded. In a preferred embodiment, this peak is formed at a radius of about 5 mm. Since the curved surface 55 of the posterior cam is complementary to the posterior face 64, it too has a most preferred radius of 30 mm.

At least the anterior end 57 of the posterior cam 55 is blunted or rounded to provide a smooth transition when the cam contacts the spine 60. The opposite posterior end of the cam 55 can also be rounded, as shown in the figures. This rounded anterior end 57 is the first portion of the posterior cam to contact the spine as the knee is flexed to the predetermined flexion angle. Nominally, the anterior end 57 will initially contact the spine 60 below the rounded posterior peak 66.

The curved posterior face 64 of the spine is curved along substantially the entire height of the spine 60. Moreover, the posterior cam 55, or more particularly the curved surface 56 of the cam, has a length that is substantially equal to the length or height of the curved face of the spine. At about 120° of flexion, the curved surface of the posterior cam is completely nested within the concave posterior face of the spine. This complementary interface can then operate as a fulcrum or pivot point for further relative rotation between the tibial and femoral components. While the condyle bearings and bearing surfaces continue to articulate relative to each other, the greater share of the shear load can now be borne by the complementary interface between the posterior cam 55 and the posterior face 64 of the spine 60. This interface can thus preserve the mechanical advantage of the quadricep muscle through high flexion angles. In addition, the kinematics of this spine/cam interface allows a patellar implant to easily follow the patellar track 49 without placing undue stress on the patellar tendons.

Referring to FIG. 4b, it can be seen that the spine 60 has an anterior-posterior dimension that is significantly less than the distance between the anterior and posterior cams 50, 55 in the cam housing 42. From the limit of extension, shown in FIG. 4a, to the normal straight leg position of FIG. 4b the spine does not contact the cam housing and therefore does not either bear any knee loads or dictate any knee motion. In one feature of the invention, the cam housing 42 is elongated with a distance between anterior and posterior cams that is significantly greater than the anterior-posterior (a-p) dimension of the spine. In a preferred embodiment, the distance between cams is about 1.5 times the a-p dimension of the spine. In one specific embodiment, the a-p dimension of the spine is about 10.0 mm at the posterior peak 66, and the distance between the anterior cam face 51 and the anterior end of the posterior cam 55 is about 15.0 mm.

With this configuration, the knee load is carried solely by the articulating interface between the condyle bearings 30, 32 and the bearing surfaces 26, 28. As the knee starts to flex from the straightened position shown in FIG. 4b the quadricep muscles enjoy their greatest moment arm and mechanical advantage. As the knee continues to flex, the femoral component 12 moves posteriorly relative to the tibial component 14 so the quadricep mechanical advantage gradually decreases.

In order to preserve the quadricep mechanical advantage, the present invention contemplates that the posterior face 64 of the spine will contact the posterior cam 55 after a pre-determined amount of flexion. In a preferred embodiment, this pre-determined amount of flexion of about 50°. At this point, the spine and posterior cam cooperate to provide an additional articulating bearing interface to not only share in the shear loads, but also to provide a fulcrum or reaction surface working against the quadricep muscle to preserve the flexion moment arm and mechanical advantage. As the flexion continues, the posterior cam 55 becomes fully seated within the concave posterior face 64 of the spine to maximize the bearing contact between these two components.

In another aspect of the invention, the stem 22 of the bearing 20 defines a central bore 70 at least partially therethrough, as shown in FIG. 4b. A stiffening pin 72 can be pressed into the bore 70, as shown in FIG. 4c. The pin 72 can be formed of a stiff metal, such as a cobalt chrome alloy.

In accordance with accepted practice, the prosthetic components designed to engage the natural bone, such as the femoral component 12 and the tibial platform 16, are formed of a biocompatible metal, such as cobalt chrome alloy. The bone engaging surfaces of these components can be textured to facilitate cementing the component to the bone, or can be porous coated to promote bone ingrowth for permanent fixation.

However, the bearing 20 is most preferably formed of a material that allows for smooth articulation and rotation between the bearing and the other components. The material is selected to meet several criteria, such as producing as little friction as possible between the articulating/rotating surfaces, providing as much wear resistance as possible, and remaining as strong as possible. One preferred material is ultra-high molecular weight polyethylene (UHMWPe) because it optimizes these three and other criteria.

One concern posed by the material used for the spine 60 is that the spine must bear significant loads in the transverse and coronal planes—i.e., lateral to the spine axis. In one approach, the spine 60 can be provided as a separate component that mates with the remainder of the bearing 20. With this approach, the spine can be formed of a high strength metal, such as the cobalt alloy mentioned above. This approach adds to the complexity of the knee construct and adds the problem of interfacing the spine to the remainder of the bearing.

It is preferred that the spine 60 be integrally formed with the bearing 20, which means that the spine will be formed of the same material. Where this material is UHMWPe, transverse or shear strength, and even bending stiffness, becomes a design consideration, particularly for active patients. To address this concern, the stiffening pin 72 can extend through the axis of the spine 60 to add bending stiffness and shear resistance to the spine. The pin 72 can be provided in different lengths depending upon the desired effect. For instance, the pin can be sized for insertion from the top of the spine 60 and to only extend for the height of the spine. Alternatively, as shown in FIG. 4c, the pin can be introduced from the bottom of the bearing stem 22 and can include a stepped diameter to be press-fit into a comparable stepped diameter bore 70 of the stem 22.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

For instance, the preferred embodiment contemplates one form of mobile bearing knee in which the tibial bearing rotates relative to the tibial platform. Other mobile bearing knees are contemplated, including knee prostheses in which the bearing slides on the platform. Of course, the inventive concepts can also be implemented in knee prosthesis in which the bearing does not move or is incorporated into the tibial platform.

In addition, the illustrated embodiments contemplate that the spine projects from the bearing. The inventive concepts can be implemented where the spine is separate from the bearing, whether as a separate insert or integrated with the tibial platform.

What is claimed is:

1. A knee prosthesis comprising:
  a femoral component configured to be attached to a distal end of a femur and having medial and lateral condyle surfaces spaced apart from each other to define a notch therebetween, said notch defining an elongated cam housing having a posterior cam at one end of said cam housing;
  a tibial component including a platform configured for attachment to a proximal end of a tibia and a bearing supported on and rotatable in relation to said platform, said bearing defining (i) medial and lateral bearing surfaces configured to articulate with said medial and lateral condyle surfaces, and (ii) a spine projecting superiorly within said cam housing when said condyle surfaces are in articulating contact with said bearing surfaces, wherein said spine defines a posterior face facing said posterior cam and configured for cooperative engagement with said posterior cam, said spine further defining a bore therethrough, and said spine further being formed of a first material, and further said cam housing defines a width sufficient to provide a clearance ranging between about 0.12 mm to about 0.50 mm on each side of said spine when said spine projects into said cam housing; and a pin configured to be disposed within said bore, said pin being formed of a second material which is different from said first material.

2. The knee prosthesis according to claim 1, wherein said pin is configured to be press-fit into said bore.

3. The knee prosthesis according to claim 1, wherein said tibial component includes:
a socket defined in said platform; and
a stem extending from said bearing configured for rotating engagement within said socket.

4. The knee prosthesis according to claim 3, wherein said bore extends into at least a portion of said stem and said pin is configured to extend into said portion of said stem.

5. The knee prosthesis according to claim 1, wherein said second material is a metallic material and said first material is a plastic material.

6. A knee prosthesis comprising:
a femoral component configured to be attached to a distal end of a femur and having medial and lateral condyle surfaces spaced apart from each other to define a notch therebetween, said notch defining an elongated cam housing having a posterior cam at one end of said cam housing; and
a tibial component including (i) a platform configured for attachment to a proximal end of a tibia, (ii) a bearing supported on and rotatable in relation to said platform, said bearing defining medial and lateral bearing surfaces configured to articulate with said medial and lateral condyle surfaces, and (iii) a spine projecting superiorly from said bearing within said cam housing when said medial and lateral condyle surfaces are in articulating contact with said bearing surfaces,
wherein said spine defines an anterior face and an opposite posterior face facing said posterior cam, said posterior face and said posterior cam defining complementary curved surfaces configured for cooperative engagement when said femoral component and said tibial component are rotated relative to at least a predetermined flexion angle,
wherein said cam housing defines a width sufficient to provide a clearance ranging between about 0.12 mm to about 0.50 mm on each side of said spine when said spine projects into said cam housing,
wherein said spine has a height of about 16.0-24.0 mm and said cam housing includes a roof and is sized relative to said condyle surfaces so that said spine cannot contact said roof when said condyle surfaces are supported on said bearing surfaces,
wherein said complementary curved surface of said posterior face of said spine is concave at a radius and has a length sized so that said curved surface extends along substantially the entire height of said spine, and
wherein said spine terminates in a rounded posterior peak.

7. A knee prosthesis comprising:
a femoral component configured to be attached to a distal end of a femur and having medial and lateral condyle surfaces spaced apart from each other to define a notch therebetween, said notch defining an elongated cam housing having a posterior cam at one end of said cam housing; and
a tibial component including (i) a platform configured for attachment to a proximal end of a tibia, (ii) a bearing supported on and rotatable in relation to said platform, said bearing defining medial and lateral bearing surfaces configured to articulate with said medial and lateral condyle surfaces, and (iii) a spine projecting superiorly from said bearing within said cam housing when said medial and lateral condyle surfaces are in articulating contact with said bearing surfaces,
wherein said spine defines an anterior face and an opposite posterior face facing said posterior cam, said posterior face and said posterior cam defining complementary curved surfaces configured for cooperative engagement when said femoral component and said tibial component are rotated relative to at least a predetermined flexion angle,
wherein said cam housing defines a width sufficient to provide a clearance ranging between about 0.12 mm to about 0.50 mm on each side of said spine when said spine projects into said cam housing,
wherein said cam housing defines an anterior cam at an opposite end thereof,
wherein said anterior face of said spine facing said anterior cam is substantially flat, and
wherein said anterior cam defines a substantially flat surface complementary to said anterior face of said spine.

8. The knee prosthesis according to claim 7, wherein said complementary curved surface of said posterior face of said spine is concave at a radius, and said complementary curved surface of said posterior cam is curved at substantially said radius.

9. The knee prosthesis according to claim 7, wherein said clearance is about 0.13 mm on either side of said spine when said spine projects into said cam housing.

10. The knee prosthesis according to claim 7, wherein said spine and said cam housing interact with each other to restrict pivoting between said femoral component and said bearing of said tibial component to between about 0.5° and 2.5°.

11. The knee prosthesis according to claim 7, wherein said spine has a height of about 16.0-24.0 mm and said cam housing includes a roof and is sized relative to said condyle surfaces so that said spine cannot contact said roof when said condyle surfaces are supported on said bearing surfaces.

12. The knee prosthesis according to claim 11, wherein said complementary curved surface of said posterior face of said spine is concave at a radius and has a length sized so that said curved surface extends along substantially the entire height of said spine.

13. The knee prosthesis according to claim 12, wherein said spine terminates in a rounded posterior peak.

14. The knee prosthesis according to claim 11, wherein said posterior cam has a length from an anterior end to a posterior end that is substantially equal to the length of said curved surface of said posterior face of said spine.

15. The knee prosthesis according to claim 7, wherein said cam housing defines an anterior-posterior distance between said curved surface of said posterior cam at said one end and an opposite end of said cam housing that is substantially greater than an anterior-posterior dimension of said spine.

16. The knee prosthesis according to claim 15, wherein the anterior-posterior distance defined by said cam housing is about 1.5 times greater than the anterior-posterior dimension of said spine.

17. The knee prosthesis according to claim 7, wherein said bearing is mounted on said platform to permit relative movement therebetween.

18. The knee prosthesis according to claim 17, wherein said tibial component further includes:
   a socket defined in said platform; and
   a stem extending from said bearing configured for rotating engagement within said socket.

* * * * *

UNITED STATES PATENT AND TRADEMARK OFFICE
CERTIFICATE OF CORRECTION

PATENT NO. : 8,382,847 B2  
APPLICATION NO. : 11/121408  
DATED : February 26, 2013  
INVENTOR(S) : Joe Wyss et al.

Page 1 of 1

It is certified that error appears in the above-identified patent and that said Letters Patent is hereby corrected as shown below:

On Title Page Item (75)

Delete "Marc C. Vosler" and insert -- Marc A. Vosler --.

Signed and Sealed this  
Twentieth Day of August, 2013

Teresa Stanek Rea  
*Acting Director of the United States Patent and Trademark Office*